United States Patent [19]
Lerman

[11] Patent Number: 5,840,050
[45] Date of Patent: Nov. 24, 1998

[54] POST-OPERATIVE HIP BRACE

[76] Inventor: Max Lerman, 1950 Carla Ridge, Beverly Hills, Calif. 90210

[21] Appl. No.: 717,841

[22] Filed: Sep. 23, 1996

[51] Int. Cl.$^6$ ...................................................... A61F 5/00
[52] U.S. Cl. .............................................. 602/19; 602/23
[58] Field of Search .............................. 602/4, 5, 12, 19, 602/23, 24; 128/DIG. 15

[56] References Cited

U.S. PATENT DOCUMENTS

| | | | |
|---|---|---|---|
| 2,753,864 | 7/1956 | Weidermann | 602/23 |
| 2,889,830 | 2/1959 | Raymond | 602/23 |
| 3,703,171 | 11/1972 | Schiavitto | 602/26 |
| 4,013,070 | 3/1977 | Harroff | 602/21 |
| 4,481,941 | 11/1984 | Rolfes | 602/19 |
| 4,569,348 | 2/1986 | Hasslinger | 128/DIG. 15 X |
| 4,905,678 | 3/1990 | Cumins | 602/19 |
| 5,058,576 | 10/1991 | Grim | 602/21 |
| 5,286,251 | 2/1994 | Thompson | 602/23 |
| 5,709,648 | 1/1998 | Webb | 602/19 |

*Primary Examiner*—Richard J. Apley
*Assistant Examiner*—Denise Pothier
*Attorney, Agent, or Firm*—Christie, Parker & Hale, LLP

[57] ABSTRACT

A post-operative hip brace for preventing hip dislocations during recovery of a patient including a waist strap and an upper leg strap that fits around the upper thigh of the patient. The two straps are spaced apart and extend generally parallel to each other, and support the top and bottom of a vertically extending thin, generally flat semi-rigid hip support for extending along the side of the hip. The hip support includes a plurality of long narrow, generally parallel, vertically-extending, horizontally spaced, semi-rigid metal stays extending between the waist strap and the upper leg strap along the side of the hip joint. The stays are malleable and can be shaped manually to a desired configuration for matching the shape of the patient's hip in the area of the surgical incision. The stays are each removable from long narrow sleeves on the support. The inside of the hip support also includes a spacer that overlies the incision to provide cushioning.

17 Claims, 2 Drawing Sheets

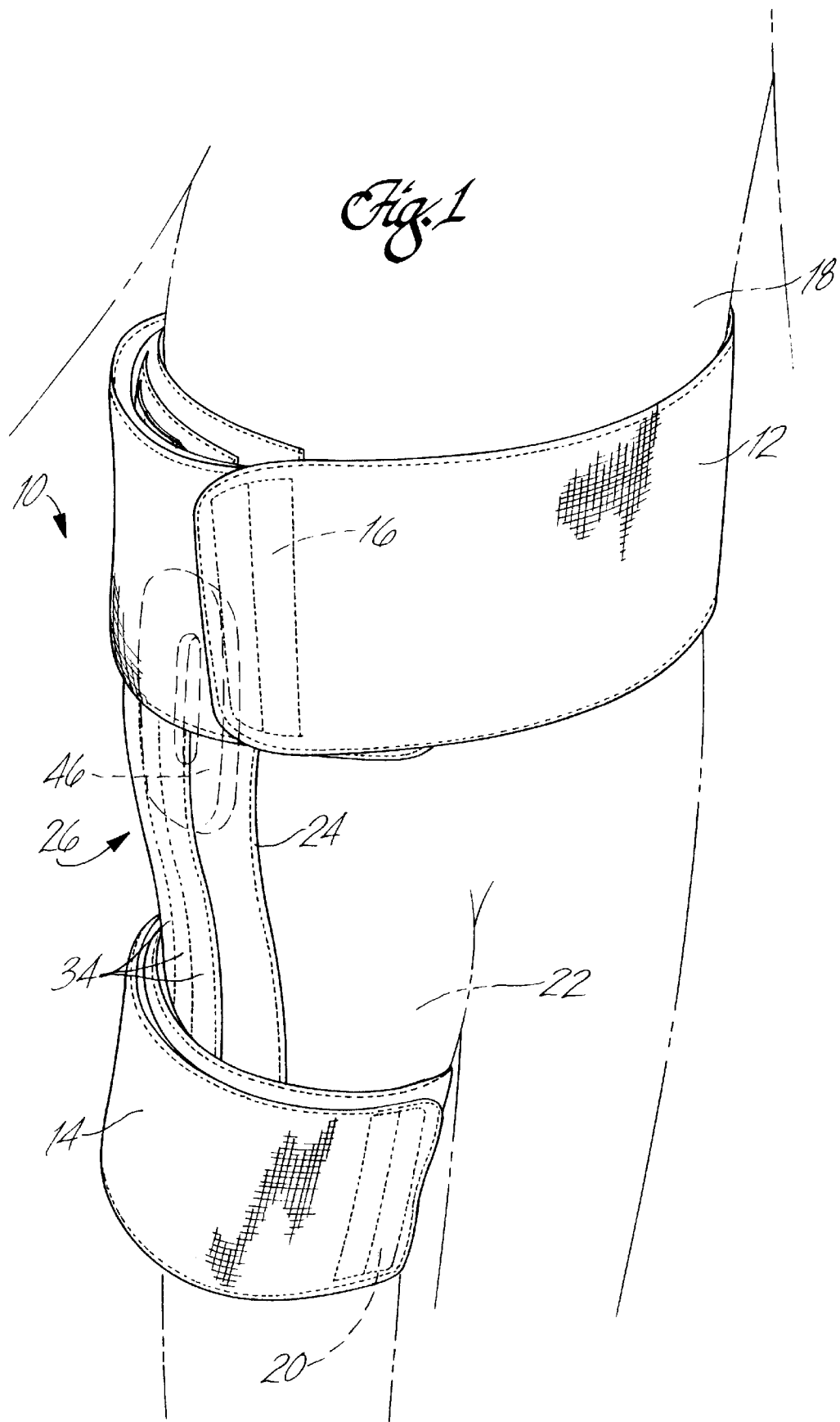

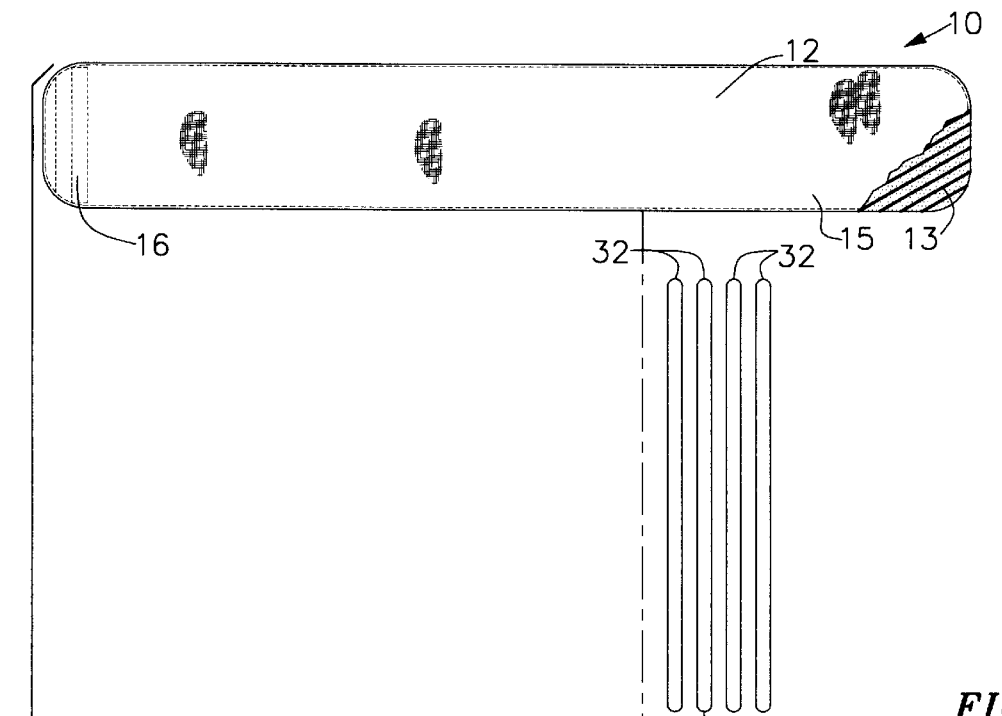
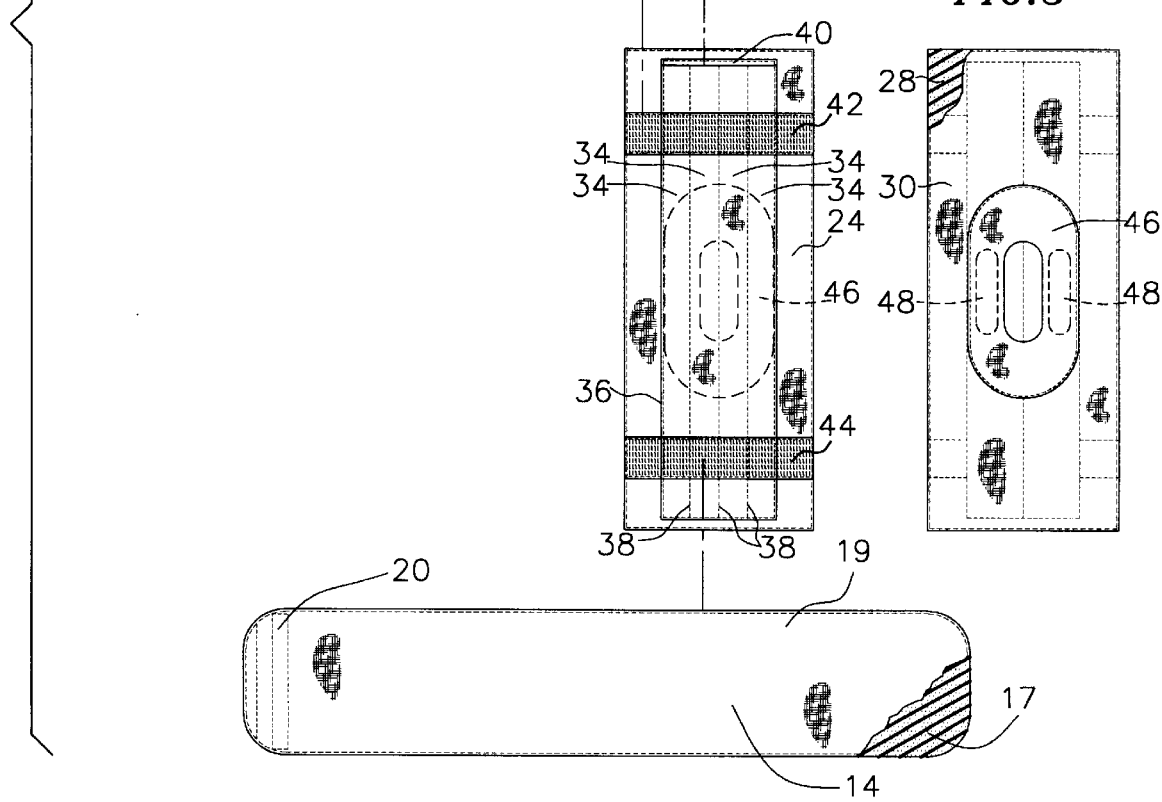

POST-OPERATIVE HIP BRACE

FIELD OF THE INVENTION

This invention relates generally to hip braces, and more particularly, to a hip brace worn temporarily after surgery to prevent dislocation of the hip from activities occurring during the healing process.

BACKGROUND OF THE INVENTION

Various hip surgery techniques are used for repairing or replacing bone structures in the pelvic and upper thigh regions of the human anatomy. Such surgery normally requires an incision of the muscle and tendon tissue adjacent to the pelvis such that the bone structure surrounded by such tissue may be accessed for replacement or repair. The muscle and tendon tissue not only facilitates movement of the skeletal hip structure but also assists in holding the thigh bone within the pelvic socket.

During recovery, the muscle and tendon tissue will be substantially weakened and not completely effective in retaining the thigh bone within the pelvic socket. Accordingly, in some cases patients recovering from hip surgery inadvertently move the thigh and dislocate the femur from the pelvic socket. Certain movements of the thigh will not cause dislocation, and thus the patient should not be completely immobilized in those circumstances, to allow some minimal exercise of the healing muscles and tendons during the very early stages of the recovery process and to accommodate some mobility by the patient. Thigh movements commonly known to cause dislocation of the femur are the exaggerated flexion of the hip such as pivoting the thigh forwardly toward the chest, or adduction of the thigh toward the other leg, or a combination of flexion and adduction such as crossing one leg over the other. In addition to causing an extreme amount of pain to the patient, hip dislocation may require the surgeon to reoperate to put the thigh bone back into the pelvic socket.

In the past certain braces have been used post-operatively to hold the patient's legs in a fixed position while the patient rests in bed for a few weeks after surgery. The patient must carefully observe certain precautions about hip movement that are to be avoided, as explained by a doctor, but in some instances these braces allow the hip to inadvertently become dislocated. Consequently, more rigid hip braces were developed to prevent hip dislocation. Prior rigid hip braces used after surgery include a long, rigid hinged bar at the side of the hip with a rotating angular limiter at the hip joint that confines angular rotation of the hip to a pre-set angle. A problem with such braces is that they are heavy, bulky, and expensive to manufacture. Another prior post-operative hip brace includes a waist belt connected to a thigh belt by flexible inelastic posterior straps, a medial strap, and anterior straps. Because the straps which connect the waist and thigh belts are flexible, this hip brace is unable to provide rigid support for patients recuperating from total hip replacement surgery.

Consequently, a need exists for a hip brace that is light weight, is not bulky, and is inexpensive to manufacture, which can be applied to a patient post-operatively, and which prevents hip adduction, hyperflexion, and twisting of the hip joint during recovery of the patient.

SUMMARY OF THE INVENTION

This invention provides a post-operative hip brace to be worn temporarily after hip surgery to prevent dislocation of the hip during the healing process. The brace includes a waist strap and an upper leg strap that fits around the upper thigh. The two straps are spaced apart and extend generally parallel to each other, and both support the top and bottom of a vertically extending thin, generally flat, semi-rigid hip support for extending along the side of the hip.

The hip support includes a group of long, narrow, generally parallel, vertically-extending, horizontally spaced apart, semi-rigid metal stays extending between the waist strap and the upper leg strap along the side of the hip joint. The stays are malleable and can be shaped manually to a desired configuration for matching the shape of the patient's hip in the area of the surgical incision. The stays are each removable from long narrow sleeves on the support.

The inside of the hip support also includes a removable spacer that overlies the incision to provide comfort to that area when the brace is in place. The brace prevents hip adduction, hyperflexion, and twisting of the hip joint during the recovery process, and as a result, hip dislocations are prevented. Even though the brace holds the patient's hip in a relatively stiff position, patient ambulation is easily possible.

These and other aspects of the invention will be more fully understood by referring to the following detailed description and the accompanying drawings.

In one embodiment, the hip support comprises a long, flat, thin flexible carrier made of fabric or the like, and the sleeves are also of a similar material and affixed to the carrier.

BRIEF DESCRIPTION OF THE DRAWINGS

FIG. 1 is a perspective view of the hip brace as worn on a patient;

FIG. 2 is an exploded elevational view of the hip brace of FIG. 1; and

FIG. 3 is a rear elevational view of the hip support component of the hip brace of FIG. 1.

DETAILED DESCRIPTION

Referring to FIGS. 1 and 2, a post-operative hip brace 10 of the present invention includes a flexible elongated waist strap 12 and a flexible, elongated upper leg strap 14 spaced apart and extending generally parallel to each other. The waist strap 12 includes a fastener 16 at one end of the strap for securing the waist strap around the waist 18 of the patient. Preferably, fastener 16 is a section of frictional hook fastener which securely attaches to the outer surface 15 of the waist strap. Other types of fasteners could also be incorporated such as snaps, buttons, etc. The outer surface of the waist strap preferably comprises a polyester knit material which readily accepts hook fastener 16 at any position along the length of the strap to accommodate various waist sizes of patients. Other types of material can be used for the outer surface of the waist strap such as nylon, cotton, etc. For materials which do not readily accept a hook fastener, sections of a frictional loop fastener can be sewn to the outer surface for securing the strap around the waist of the patient.

Similarly, upper leg strap 14 includes a fastener 20 positioned at one end of the strap for rigidly attaching the upper leg strap around the upper thigh 22 of the patient. Fastener 20 is also a strip of a frictional hook material fastenable along any location of the outer surface 19 of strap 14. The outer surface of strap 14 is similarly a polyester knit material which readily accepts fastener 20 at any position along the surface to accommodate any thigh circumference for various patients. Straps 12 and 14 include a polyurethane foam interior 13 and 17 respectively, to provide a soft and cushioning effect for the straps when fastened to the body. Fasteners 16 and 20 are preferably sewn onto the surface of straps 12 and 14. Alternatively, fasteners 16 and 20 can be attached by adhesive or other suitable attachment mechanisms.

A rectangular hip support 24 extends vertically between straps 12 and 14 along the side of the hip 26 of the patient. Hip support 24 includes a polyurethane foam core 28 sewn inside a polyester knit covering 30, similar to the waist and upper leg straps 12 and 14, as shown in FIG. 3. This forms a generally flat, rectangular flexible carrier extending between the waist and upper leg straps. Hip support 24 also includes a group of preferably four long, flat, narrow, generally parallel, vertically-extending, horizontally spaced apart, semi-rigid metal stays 32 extending between the waist strap and the upper leg strap along the side of the hip joint 26. The stays are malleable and can be shaped manually to a desired. configuration for matching the shape of the patient's hip in the area of the surgical incision. The stays, when shaped, hold their shaped position during use. Preferably, the stays 32 are aluminum; however, any lightweight malleable semi-rigid material such as composite plastics or rubber may be used.

The stays 32 are positioned on the outside surface of the flexible carrier portion of the hip support 24 by sleeves 34 sewn to the exterior surface of hip support 24. Preferably, the sleeves 34 consist of a single piece of canvas sewn along its perimeter to the hip support, and then forming individual long, narrow side-by-side pockets by stitching a plurality of vertical rows 38 spaced horizontally across the width of the sleeve 34 to define individual pockets for the stays 32. Stays 32 are removably placed within sleeves 34 through an opening 40 at the top of each sleeve 34.

The portion of the hip support provided by the carrier and the sleeves is flexible, and the stays, which are fixed in place in the sleeves, provide the necessary rigidity and resistance to patient movement. The stays, are each rigid torsionally, longitudinally, and laterally (to prevent bending in the normal flat plane of the stay). Their malleability permits bending to a desired shape only in a direction perpendicular to the normal flat plane of the stays.

In a preferred embodiment, each stay is about 20 inches long, about 11/16 inches wide, and its thickness varies from about 1/16 inch along the outer edges to about 1/8 inch along its central portion. The canvas piece that forms the sleeves is about 5½ inches wide, and the stays are uniformly spaced apart across the hip support.

The semi-rigid stays are located in fixed positions within the hip support when attached to the body by the waist strap and upper leg strap. The stays cooperate to prevent movement of the hip joint toward the body, they prevent flexion or rotation of the upper leg about the hip joint, and they prevent twisting of the hip joint, during recovery of the patient. Although the brace holds the patient's hip in a relatively stiff position, the brace does not prevent the patient from the minimal amount of acceptable hip movement in a restricted walking gait during the convalescent period.

Hip support 24 includes an upper fastener 42 and a lower fastener 44 for rigidly attaching hip support 24 to waist strap 12 and upper leg strap 14. Fasteners 42 and 44 are strips of hook fasteners sewn to the outer surface of the hip support across sleeves 36. Hip support, waist strap, and upper leg strap are detachable to accommodate various size components to be utilized depending upon the exact anatomical dimensions of the patient.

As shown in FIG. 3, an incision spacer 46 is positioned on the inside surface of the hip support. The spacer is a donut-shaped pad having a polyurethane foam core and a polyester knit covering having hook fasteners 48 for attaching the incision spacer to the hip support 24. This spacer is positioned on the hip support so that it overlies the incision to provide comfort to the incision when the brace is in place on the wearer.

The brace is worn temporarily, for about two to three weeks, after surgery to prevent dislocation of the hip joint, yet it is lightweight and extremely comfortable for the patient.

Although the present invention has been described and illustrated with respect to a preferred embodiment thereof, it is to be understood that it is not to be so limited since changes and modifications may be made therein which are within the full intended scope of the invention as hereinafter claimed.

What is claimed is:

1. A post-operative hip brace for preventing hip dislocation during recovery of a patient comprising:

a waist strap adjustably positionable around the waist of the patient;

a leg strap adjustably positionable above the knee around the upper leg of the patient;

a vertically extending, generally flat hip support connected between the waist strap and the leg strap; and a plurality of vertically extending and horizontally spaced apart malleable stays each removably contained on an exterior surface of the hip support, extending across the width of the patient's hip region and shaped to a configuration to match the shape of the patient's hip region in the area traversed by the spaced apart stays, the stays extending along the outside of the patient's upper leg and terminating at lower ends adjacent the leg strap spaced above the knee joint, the stays extending across the width of the patient's upper leg and shaped to a configuration to match the upper leg configuration traversed by the spaced apart stays, the stays retaining their shaped configuration and providing a level of rigid support for cooperating to resist hip adduction and flexion of the upper leg about the hip joint while allowing free bending of the knee joint to permit walking by the patient.

2. The hip brace of claim 1 wherein the stays are aluminum.

3. The hip brace of claim 1 wherein each stay is removably contained on the hip support by a sleeve located on an exterior surface of the hip support.

4. The hip brace of claim 3 wherein the sleeve contains an opening for insertion and removal of the stays.

5. The hip brace of claim 1 wherein the waist strap is adjustably positionable around the waist by incorporating a fastening means located on one end of the strap engagable along the entire length of the strap.

6. The hip brace of claim 1 wherein the leg strap is adjustably positionable around the upper leg of the patient by incorporating fastening means located on one end of the strap engagable along the entire length of the strap.

7. The hip brace of claim 1 wherein the brace further comprises a positionable spacer located on the hip support for providing a cushion for an incision on the patient.

8. An above knee brace for preventing hip adduction, hyperflexion, and twisting of a hip joint comprising:

a waist strap adjustably positionable around the waist of the patient;

a leg strap adjustably positionable above the knee around the thigh of the patient;

a hip support connected between the waist strap and the leg strap and having a plurality of vertically extending and horizontally spaced apart generally flat malleable stays each removably attached to an outer surface of the hip support, extending across the width of the patient's hip region and shaped to a configuration to match the shape of the patient's hip region in the area traversed by the spaced apart stays, the stays extending along the outside of the patient's thigh and terminating at lower ends adjacent the leg strap spaced above the knee joint, the stays extending across the width of the patient's thigh and shaped to a configuration to match the configuration of the thigh region traversed by the spaced apart stays; and means for securing the waist strap and leg strap to the waist and thigh for thereby securing the hip support and the stays along the side of the hip extending solely along the region of the upper thigh above the knee joint, the stays retaining their shaped configuration and providing a level of rigid support for cooperating to resist hip adduction, hyperflexion and twisting of the hip joint while allowing free bending of the knee joint to permit walking by the patient.

9. The brace of claim 8 wherein the means for securing the hip support along the side of the hip comprises a first strap secured to an upper portion of the hip support and adjustably positionable around the waist of a user, and a second strap secured to a lower portion of the hip support adjustably positionable around an upper leg of the user.

10. The brace of claim 9 wherein the first strap is adjustably positionable around the waist by incorporating a fastening means located on one end of the strap engagable along the entire length of the strap.

11. The brace of claim 9 wherein the second strap is adjustably positionable around the upper leg of the patient by incorporating fastening means located on one end of the strap engagable along the entire length of the strap.

12. The brace of claim 9 wherein the stays are aluminum.

13. The brace of claim 8 wherein each stay is removably contained on the hip support by a sleeve located on an exterior surface of the hip support.

14. The brace of claim 13 wherein the sleeve contains an opening for insertion and removal of the stays.

15. The brace of claim 8 wherein the brace further comprises a positionable spacer located on the hip support for providing a cushion for an incision on the patient.

16. A hip brace for preventing hip dislocation during recovery of a hip surgery patient comprising:

a waist strap adjustably positionable around the waist of the patient;

a leg strap adjustably positionable above the knee around the upper leg of the patient;

a hip support connected between the waist strap and the leg strap and having a plurality of vertically extending and horizontally spaced, malleable flat stays contained within individual pockets on an exterior surface of the hip support and configured to match the shape of the patient's hip region, the stays sized to extend along the outside of the patient's upper leg and terminating at lower ends adjacent the leg strap spaced above the knee joint, the stays sized to extend across the width of the patient's upper leg and shaped to a configuration to match the upper leg configuration traversed by the spaced apart stays; and a spacer for providing a cushioning effect for an incision, the spacer having an opening for receipt of the incision, the stays retaining their shaped configuration and providing a level of rigid support for cooperating to resist hip adduction, hyperflexion and twisting of the hip joint while allowing free bending of the knee joint to permit walking by the patient.

17. The hip brace of claim 16 wherein the pockets contain an opening for insertion and removal of the stays.

* * * * *

UNITED STATES PATENT AND TRADEMARK OFFICE
CERTIFICATE OF CORRECTION

PATENT NO. : 5,840,050
DATED : November 24, 1998
INVENTOR(S) : Max Lerman

It is certified that error appears in the above-identified patent and that said Letters Patent is hereby corrected as shown below:

On the title page,
Item [56] References Cited, U.S. Patent Documents change
"2,889,830 2/1959 Raymond .. 602/23" to
-- 2,889,830 6/1959 Raymond .. 602/23 --.
Column 3, line 20, after "desired" delete the period.
Column 3, line 39, after "The stays" delete the comma.
Column 3, line 45, replace "11/16 inches" with --11/16 inch --.
Column 4, lines 33,37,39, replace "extending" with -- sized to extend -- (all occurrences).
Column 4, line 57, replace "engagable" with -- engageable --.
Column 4, line 62, replace "engagable" with -- engageable --.
Column 5, lines 9,12,15,21, replace "extending" with -- sized to extend -- (all occurrences).
Column 5, line 36, replace "engagable" with -- engageable --.
Column 6, line 2, replace "engagable" with -- engageable --.

Signed and Sealed this

Twenty-third Day of November, 1999

*Attest:*

Q. TODD DICKINSON

*Attesting Officer*          *Acting Commissioner of Patents and Trademarks*